(12) United States Patent
Powell et al.

(10) Patent No.: US 6,355,005 B1
(45) Date of Patent: Mar. 12, 2002

(54) ARTICULATED GUIDEWIRE

(75) Inventors: Ferolyn T. Powell, San Carlos; Larry Rogers, Half Moon Bay; Ron Ray Hundertmark, San Mateo; Charles Milo, Union City, all of CA (US)

(73) Assignee: Devices for Vascular Intervention, Inc., Redwood City, CA (US)

( * ) Notice: Subject to any disclaimer, the term of this patent is extended or adjusted under 35 U.S.C. 154(b) by 0 days.

(21) Appl. No.: 09/038,784

(22) Filed: Mar. 9, 1998

Related U.S. Application Data (62) Division of application No. 08/557,234, filed on Nov. 14, 1995, now Pat. No. 5,868,685.

(51) Int. Cl.[7] ................................. A61B 5/00
(52) U.S. Cl. .................. 600/585; 604/434; 604/466
(58) Field of Search ................. 600/585, 433, 600/434; 604/95, 96, 280, 281, 282

(56) References Cited

U.S. PATENT DOCUMENTS

| | | | |
|---|---|---|---|
| 4,979,951 A | 12/1990 | Simpson | |
| RE33,569 E | 4/1991 | Gifford | |
| 5,071,425 A | 12/1991 | Gifford, III et al. | |
| 5,368,592 A | * 11/1994 | Stern et al. | ................. 604/95 |
| 5,385,152 A | * 1/1995 | Abele et al. | ................. 600/585 |
| 5,964,016 A | * 11/1995 | Nicholas et al. | .............. 600/585 |
| 5,499,632 A | 3/1996 | Hill, III et al. | |

\* cited by examiner

*Primary Examiner*—Cary O'Connor
*Assistant Examiner*—Pamela L. Wingood
(74) *Attorney, Agent, or Firm*—Peninsula IP Group; Douglas A. Chaikin (57) ABSTRACT

Disclosed herein is an articulated guidewire for insertion into a blood vessel. The articulated guidewire includes a rotatable sensor cable, a sensor, a connector, and a satellite wire. The sensor cable has a proximal end and a distal end. A sensor connects to the sensor cable near the distal end and rotates with the sensor cable. The satellite wire attaches to the distal end of the sensor cable and holds the sensor cable in the blood vessel. The connector includes a ball and socket joint which aligns the satellite wire and the sensor cable at a variable angle.

17 Claims, 6 Drawing Sheets

ARTICULATED GUIDEWIRE

This application is a divisional of U.S. Nonprovisional Patent Application No. 08/557,234, now U.S. Pat. No. 5,868,685 filing date Nov. 14, 1995.

BACKGROUND OF THE INVENTION

1. Field of the Invention

This invention relates to guidewires for use in biological conduits. More particularly this invention relates to guidewires which are articulated for rotating a sensor.

2. Previous Art

Atherosclerosis, a common vascular disease, is characterized by undesired deposits of material on the interior of an artery. These deposits include atheroma which is formed from a range of matter from soft fatty material to hard calcified tissue. Atheroma may occlude the artery and restrict blood flow. In some cases, restricted blood flow causes severe complications including strokes and heart attacks.

Recently, much research focuses on treatments for atherosclerosis. One successful treatment is a surgical procedure known as atherectomy. Atherectomy procedures generally restore blood flow in occluded arteries by reducing the size of atheroma. During an atherectomy, a catheter is inserted into the vasculature through an incision made, for example, in the femoral artery of a patient. The catheter slides through the vasculature of a patient to an occluded region where an atheroma is formed.

A small cutter is disposed within the atherectomy catheter. When the catheter is properly inserted into the vasculature, the cutter aligns with an atheroma. The cutter rotates and translates, removing the atheroma in small pieces. The catheter retains the small pieces. Removal of the catheter with the small pieces of atheroma completes the atherectomy procedure. An example of the atherectomy catheter is disclosed by Gifford III et al. in U.S. Pat. No. 5,071,425, the disclosure of which is incorporated herein by reference.

Undesirable deposits (e.g. deposits which cause occlusion) may also form in various biological conduits such as within the urinary tract. Devices and techniques used for atherectomy procedures are adapted in size, flexibility and operation to remove the undesirable deposits from various biological conduits. For example, work elements such as cutters, sensors and other diagnostic devices can be adapted for specific use in various biological conduits.

The location of an occlusion in a biological conduit must be precisely identified. This is accomplished through various diagnostic techniques such as fluoroscopy. With the location of an undesirable deposit identified, a guidewire is inserted into the biological conduit. In the case of atherectomy, for example, the guidewire inserts into the vasculature via the femoral artery. The guidewire slides through the biological conduit to a position distal the undesirable deposit (e.g. atheroma). With the guidewire in place, the catheter device is inserted into the biological conduit over the guidewire and follows the path of the guidewire by tracking over the guidewire. The catheter tracks over the guidewire until the cutter of the catheter aligns with the undesirable deposit.

Precise positioning of the catheter in the vasculature is necessary to perform an atherectomy. To facilite precise positioning, some catheter devices include a sensor. The catheter moves within the vasculature until the sensor detects the location of the atheroma which is desired to be removed.

A sensor may be mounted on the work element or other part of the catheter device, for example. During use, the sensor typically determines the exact location of the catheter device relative to an undesired deposit. The sensor may also determine characteristics such as the geometry and density of an undesirable deposit which is to be removed. The sensors communicate such characteristics via the catheter device to a display system. An operator (i.e., surgeon) then relies upon the display system to properly align the catheter with the undesired deposit. An example of an atherectomy catheter which employs a sensor mounted on a cutter is described by Leary et al. in U.S. Pat. No. 5,024,234, the disclosure of which is incorporated herein by reference.

The vasculature is often sensitive to catheter insertion. Catheters having a work element and a sensor may have a relatively large diameter which may injure the interior of a blood vessel. In rare cases, a risk of injury to a patient is needlessly created when a surgeon inserts an atherectomy catheter with a sensor into a patient only to find that an atherectomy is not necessary to perform. Accordingly, it is desired to operate a sensor independently of a catheter device so that a determination as to the necessity of removing deposits from an occluded blood vessel can be made prior to insertion of the catheter device into the vasculature. What is also desired is a way of precisely positioning a guidewire within a biological conduit to facilitate precise insertion of a catheter device. What is also desired is a way to monitor the effectiveness of an atherectomy procedure after an atherectomy catheter is removed.

SUMMARY AND OBJECTS OF THE INVENTION

Various objects of the present invention are provided for the purpose of facilitating an understanding of the present invention. The various objects and those which will become apparent are illustrative only and are not to be understood to limit the scope of the appended claims.

It is an object of the present invention to provide an articulated guidewire which is capable of intravascular imaging.

It is another object to provide a device having a sensor, the device being adapted for insertion into a biological conduit such as a blood vessel prior to insertion of a catheter.

It is another object to provide a device which inserts through a catheter device and rotates a sensor to facilitate intravascular imaging during operation of the catheter.

It is yet another object to provide a device having a sensor, the device being removable from a blood vessel either before, during or after removal of the catheter.

To accomplish these objects and those that will be mentioned and will become apparent below, a guidewire for insertion into a biological conduit comprises:

a sensor cable having a proximal end and a distal end, the sensor cable being capable of attachment to a sensor;

a satellite wire for holding the sensor cable in a biological conduit;

a connector for connecting the distal end of the sensor cable to the satellite wire, the connector being flexible for allowing the sensor cable to rotate with respect to the satellite wire, whereby, when the satellite wire holds the sensor cable in a biological conduit, the sensor cable rotates with respect to the satellite wire.

In a preferred embodiment, the connector includes a ball and a socket which interconnect to form a ball and socket joint. The socket is attached to the distal end of the sensor cable. The ball is attached to the satellite wire.

In another preferred embodiment, the connector includes a ball and a socket which interconnect to form a ball and socket joint. The socket attaches to the satellite wire. The ball attaches to the distal end of the sensor cable.

In another preferred embodiment, the sensor cable is electrically conductive and a sensor attaches adjacent to the distal end of the sensor cable. In a variation of this embodiment the sensor is formed from a single crystal which is embedded in the sensor cable. In another variation of this embodiment, the sensor is an ultrasonic imaging transducer. In another variation of this embodiment, the sensor is a PVDF transducer.

In another preferred embodiment, the guidewire inserts into a blood vessel and the satellite wire extends from the connector along the blood vessel. The satellite wire and holds the distal end of the sensor cable when the sensor cable rotates.

An advantage of the present invention is that the articulated guidewire inserts into a biological conduit to determine whether subsequent catheter insertion is necessary.

Another advantage of the present invention is that the articulated guidewire operates independently of the catheter to permit imaging before, during, and after an invasive procedure such as atherectomy.

Another advantage of the present invention is that the articulated guidewire, when used with a catheter, can be removed after the catheter to inspect the blood vessel interior after an aggressive procedure such as atherectomy and to evaluate the post-atherectomy condition of the blood vessel.

BRIEF DESCRIPTION OF THE DRAWINGS

For a further understanding of the objects and advantages of the present invention, reference should be had to the following detailed description, taken in conjunction with the accompanying drawings, in which like parts are given like reference numerals and wherein.

DETAILED DESCRIPTION

Figure 1:
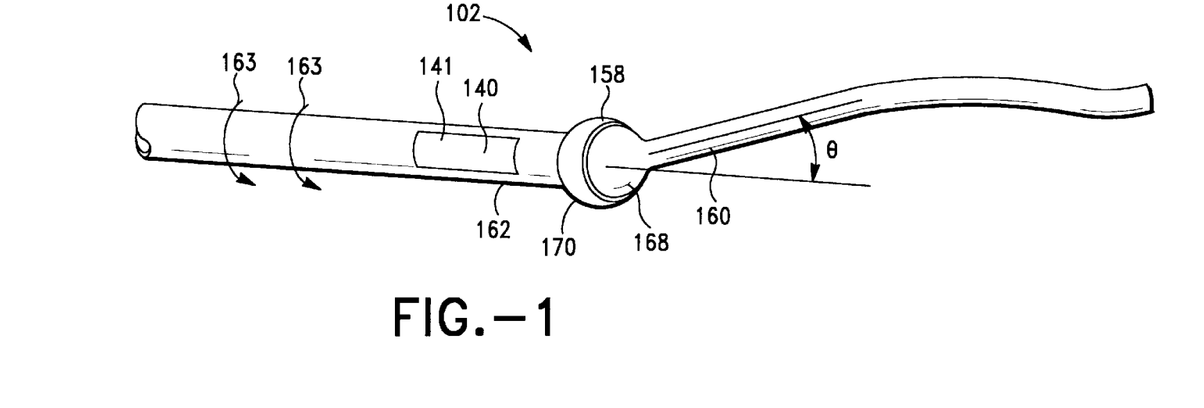
FIG. 1 is a perspective view of an articulated guidewire in accordance with the present invention.

With particular reference to FIG. 1, an articulated guidewire generally designated 102 is shown. The word "articulated" as used herein means an interconnection of parts by a flexible joint which permits relative movement between the interconnected parts. The articulated guidewire 102 includes a sensor cable 162, a sensor 140, a connector 158 and a satellite wire 160. The sensor cable 162 is rotatable in the direction of the arrows 163.

The connector 158 includes a ball and socket joint having a ball 168 and a socket 170. The ball 168 is formed having an external diameter within the range of 0.018–0.026 inches. The socket 170 is formed having an internal diameter slightly greater than the external diameter of the ball 168.

Preferably, the socket has an internal diameter within the range of 0.022–0.028 inches. Accordingly, the ball 168 fits within the socket 170. The sensor cable 162 and the satellite wire 160 align at a variable angle Θ. The sensor cable 162 is has a diameter within the range of 0.016–0.024 inches. The satellite wire 160 has a diameter within the range of 0.010–0.014 inches. Depending on the desired use of the articulated guidewire 102, the dimensions of the sensor cable 162, the satellite wire 160 and for the connector 158 can be larger or smaller as necessary.

The connector 158, the ball 168 and the socket 170 are fabricated from a biologically inert material, for example, nickel titanium alloy or stainless steel. The ball 168 and the socket 170 include a suitable coating to regulate friction between the ball 168 and the socket 170. Teflon is an example of a suitable coating.

The sensor 140 attaches to the sensor cable 162. In one embodiment, the sensor 140 attaches to the sensor cable by appropriate bonding techniques such as techniques which rely upon cements or adhesives. In another embodiment, the sensor 140 is embedded in the sensor cable 162.

The sensor cable 162 rotates the sensor 140 over a circular path. In one embodiment, the sensor cable 162 rotates at an angular rate within the range of 100 to 5,000 revolutions per minute. A rate of 2000 revolutions per minute is preferred.

The sensor cable 162 is electrically conductive. The sensor 140 electronically communicates with an appropriate electronic system via the sensor cable 162. In one embodiment, the sensor cable 162 is fabricated from an electrically conductive material. In another embodiment, the sensor cable 162 includes at least one solid conductive wire. Various sensor cables 162 which are electrically conductive in accordance with the present invention include those marketed by Advanced Cardiovascular Systems, Inc. of Santa Clara, Calif.

The sensor 140 includes an ultrasonic imaging transducer 141 which emits and receives ultrasonic energy radially from the articulated guidewire 102. The sensor 140 is fabricated from a single crystal. In one embodiment, the single crystal is formed of a suitable material such as quartz, lithium niobate, lithium titanate and zinc oxide or of one of the piezoelectric ceramics such as lead titanate zirconate and barium titanate. In another embodiment, the sensor is a PVDF ultrasonic sensor.

Figure 2:
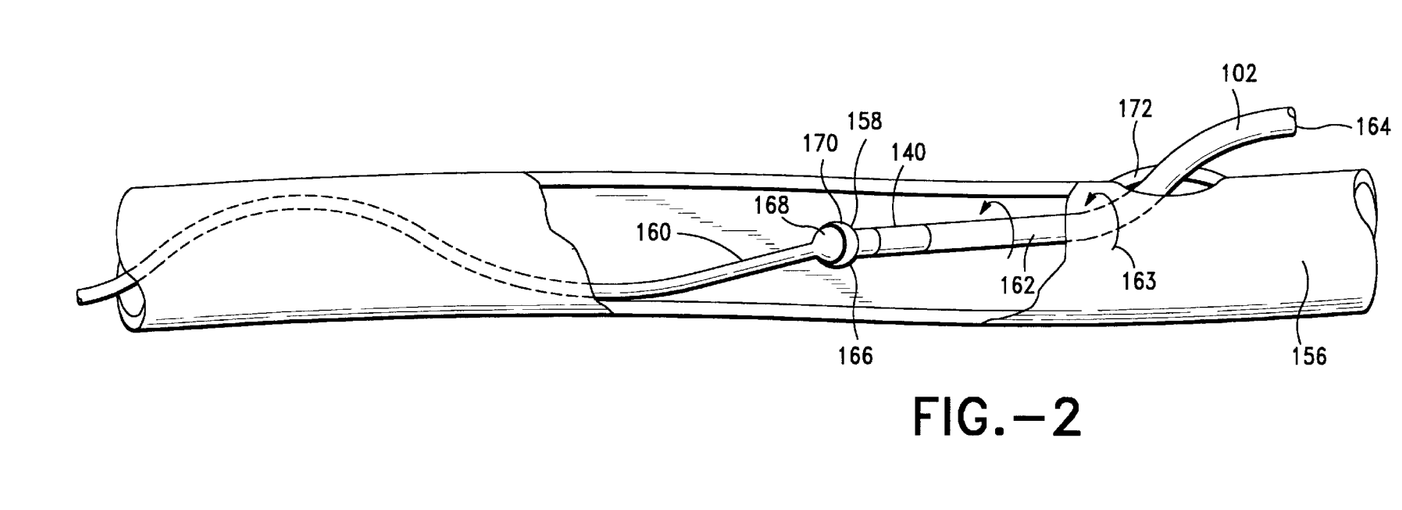
FIG. 2 is a partial cross-sectional view of the articulated guidewire of FIG. 1 inserted into a biological conduit.

With particular reference to FIG. 2, there is shown the articulated guidewire in a biological conduit. The biological conduit is a blood vessel 156. A slit 172 formed in the blood vessel 156 receives the articulated guidewire 102.

The sensor cable 162 includes a proximal end 164 and a distal end 166. The sensor 140 attaches to the sensor cable 162 near the distal end 166. The connector 158 interconnects the distal end 166 of the sensor cable 162 with the satellite wire 160 at a variable angle. The sensor cable 162 rotates the sensor 140 independently of the satellite wire 160. During rotation of the sensor cable 162, the satellite wire 160 holds the sensor 140 in a position relative to the blood vessel 156 to minimize lateral and axial movement between the sensor 140 and the blood vessel 156.

Accordingly, the satellite wire 160 holds the sensor cable 162 and permits rotation of the sensor cable 162 and the sensor 140 adjacent a desired region of the biological conduit.

Figure 3:
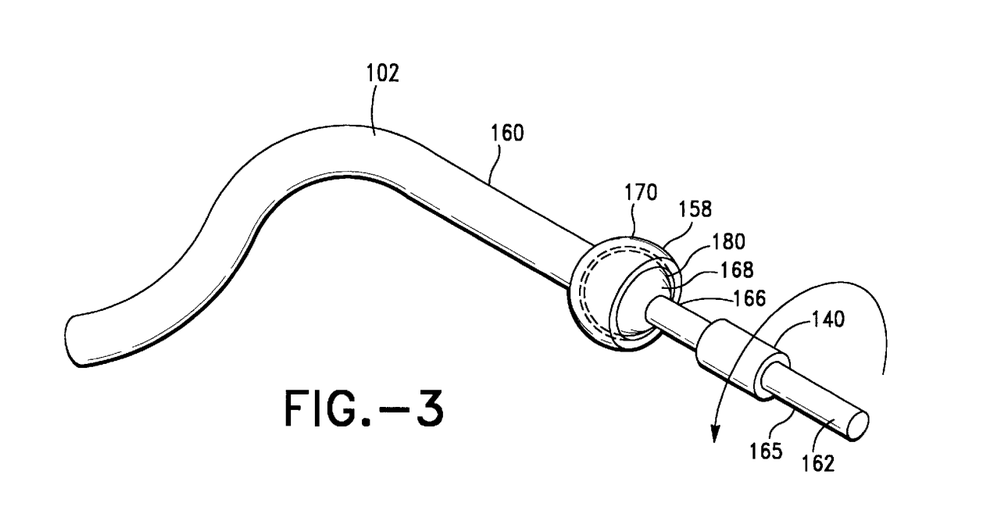
FIG. 3 is a perspective view of an embodiment of the articulated guidewire of FIG. 1.

With particular reference to FIG. 3, there is shown one embodiment of the connector 158 of the articulated guidewire 102. The connector 158 includes a ball 168 and a socket 170. The ball 168 is formed at the distal end 166 of the sensor cable 162. The socket 170 is formed at the proximal end of the satellite wire 160. The ball 168 and socket 170 interconnect to permit rotation of the sensor cable 162 with respect to the satellite wire 160.

The sensor 140 attaches adjacent to the distal end 166 of the sensor cable 162. The sensor 140 has a cylindrical shape and circumscribes the sensor cable 162. The sensor 140 creates an annular ridge which extends beyond the surface 165 of the sensor cable 162.

Figure 4:
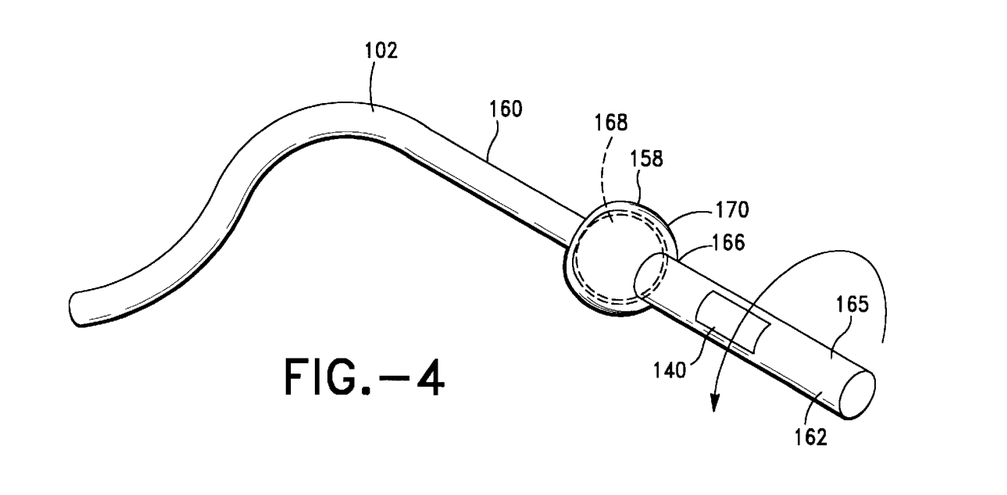
FIG. 4 is a perspective view of an embodiment of the articulated guidewire of FIG. 1.

With particular reference to FIG. 4, there is shown another embodiment of the connector 158. The connector 158 includes a ball 168 and socket 170. The ball 168 attaches to the distal end 166 of the sensor cable 162. The socket 170 attaches to the satellite wire 160. The sensor 140 has a rectangular shape. The sensor 140 is embedded in the sensor cable 162 and conforms to lie co-radially with the surface 165 of the sensor cable 162.

It will be appreciated that although a connector 158 having a ball and socket joint is disclosed, a variety of other suitable connectors which rotate and permit variable angular alignment between the sensor cable 162 and the satellite wire 160 may be used. For example, a suitable connector which has a disk shaped geometry, instead of a ball, may be employed in accordance to the present invention.

Figure 5:
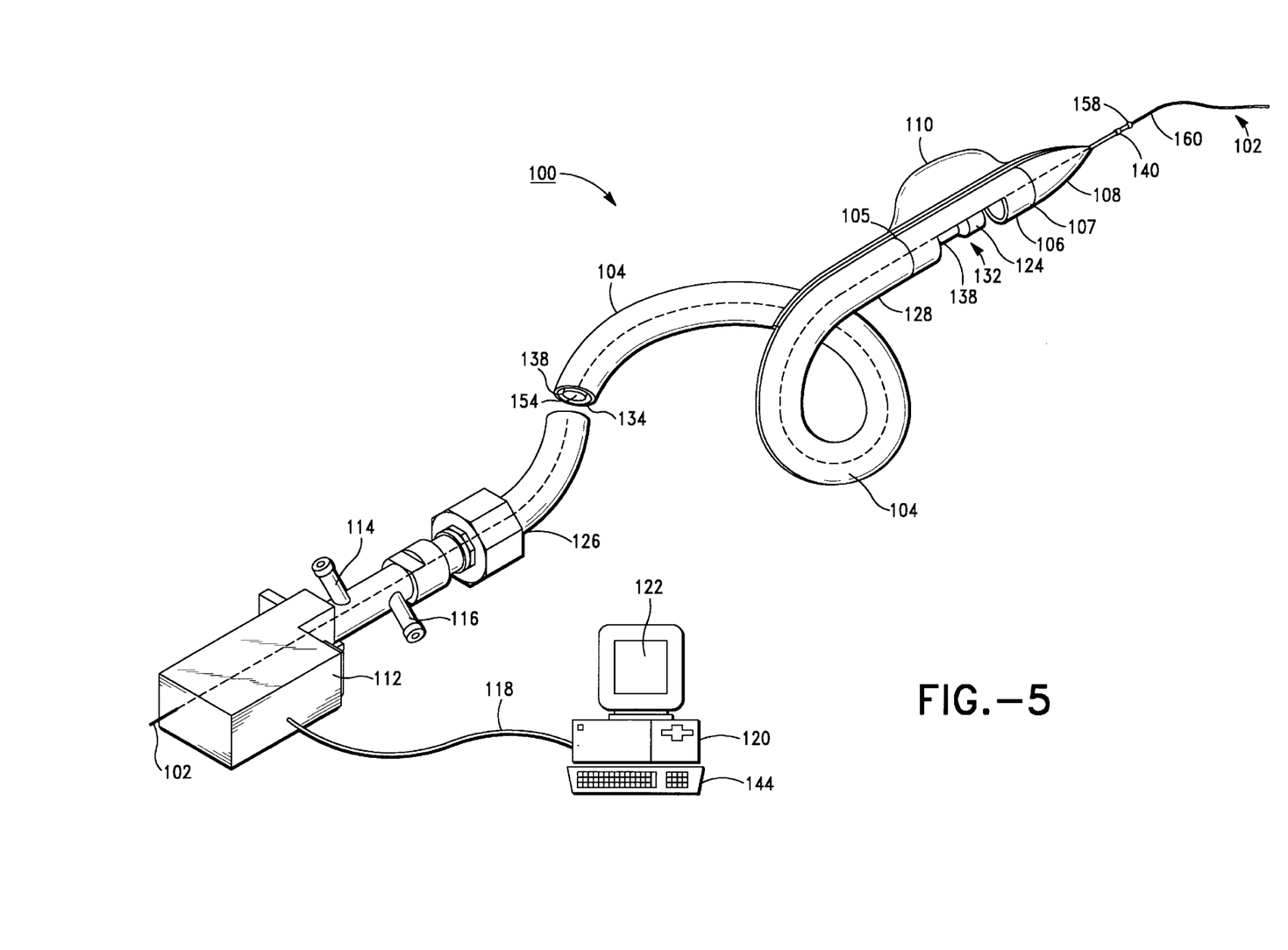
FIG. 5 is a perspective view of the articulated guidewire of FIG. 1 with catheter device.

With particular reference to FIG. 5, the imaging guidewire 102 is shown extending through a catheter device generally designated by the reference numeral 100. The catheter device 100 includes, a catheter body 104, a drive unit 112, a torque cable 138, an instrumentation cable 118, a programmed general purpose computer 144 and a display unit 122. The catheter body 104 has a proximal end 126 and a distal end 128, a housing 106, a nosecone 108, an inflatable balloon 110, an infusion port 114, an infusion port 116 and a cutter 124. General considerations relating to the design and construction of atherectomy catheters are described in U.S. Pat. Nos. 4,979,951 and 5,092,873 and Re. 33,569, the disclosures of which are incorporated herein by reference.

The proximal end 126 of the catheter body 104 connects with the drive unit 112. The housing 106 attaches to the distal end 128 of the catheter body 104. The cutter 124 is housed in the housing 106. The cutter 124 is adapted for cutting atheroma from the interior of a blood vessel. The balloon 110 attaches along the housing 106 to hold the housing 106 in a desired position within a blood vessel when the balloon 110 inflates. The flexible nosecone 108 attaches to the housing 106 and guides the catheter body 104 through a biological conduit such as a blood vessel.

The articulated guidewire 102 extends through the catheter body 104 at least to between the proximal end 126 and the distal end 128. Near the proximal end 126 of the catheter body 104, the drive unit 112 is attached to the articulated guidewire 102 for rotating the articulated guidewire 102. The articulated guidewire 102 electronically connects with the computer 144 and the display unit 122 via the instrumentation cable 18. Near the distal end 128 of the catheter body 104, the articulated guidewire 102 extends beyond the nosecone 108 of the housing 106.

The housing 106 of the catheter device 100 includes a proximal end 105, a distal end 107, and an opening. The opening is generally designated by the reference numeral 132. The opening 132 permits the housing 106 to invaginate undesired deposits (e.g. atheroma) which are to be removed. The inflatable balloon 110 is disposed along a lateral side of the housing 106 opposite the opening 132 for adjustably positioning the housing 106 within a blood vessel.

The catheter body 104 defines an internal lumen 134 which extends axially through catheter body 104. The torque cable 138 aligns coaxially along the catheter body 104 through the lumen 134 and interconnects the drive unit 112 with the cutter 124. The torque cable 138 includes a guidewire conduit 154 for tracking over the guidewire 102. The articulated guidewire 102 moves independently of the torque cable 138.

The drive unit 112 is adapted for rotating the articulated guidewire 102. In one embodiment, the drive unit 112 includes a mechanism such as an electric motor (not shown) for rotating the articulated guidewire 102. In another embodiment, the drive unit 112 is manually operable. In another embodiment, the guidewire is manipulated by a guidewire controller such as is disclosed in commonly assigned co-pending U.S. Pat. No. 5,499,632 issued Mar. 19, 1996 to Hill et al., entitled "Guidewire Migration Controller" and the continuation-in-part application Ser. No. 08/531,145 file Sep. 18, 1995. (Attorney Docket DEVI 1457), the disclosure of which is incorporated herein by reference.

Figure 6:
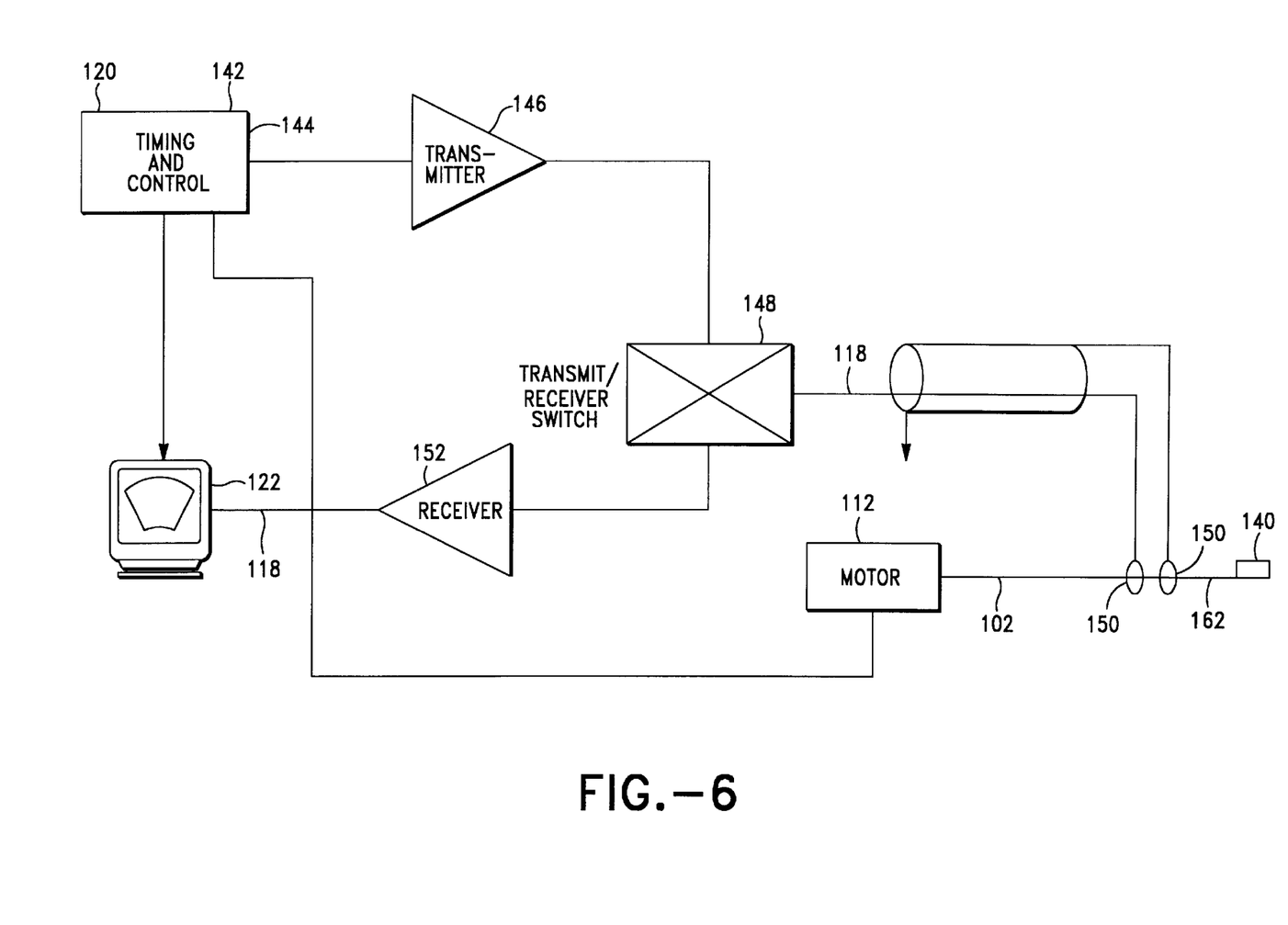
FIG. 6 is a schematic diagram of a signal processing unit of the catheter device of FIG. 5.

With particular reference to FIG. 6, there is shown a schematic diagram of various electrical components of the catheter device 100 (FIG. 5). The electrical components include timing and control circuitry 142, a transmitter 146, a transmit/receiver switch 148, a receiver 152, the display 122, slip rings 150 and the drive unit 112. The timing and control circuitry 142 is housed in the computer 144 (FIG. 5). The timing and control circuitry 142 controls the drive unit 112 for rotating the sensor 140. The timing and control circuitry 142 regulates sensor 140 operation. The slip rings 150 circumscribe the sensor cable 162 to electronically communicate with the sensor 140. The timing and control circuitry 142 electronically connects to the sensor 140 via transmitter 146, transmit/receive switch 148, instrumentation cable 118, and slip rings 150.

The computer 144 generates an output signal which is transmitted to the sensor 140. Responsive to the output signal of the computer 144, the sensor 140 emits ultrasonic energy. The emitted energy radiates outward from the sensor 140 to an area to be sensed such as blood vessel walls and atheroma, for example. The area to be sensed reflects the radiated energy back to the sensor 140. The sensor 140 receives and converts the reflected energy into a corresponding electrical signal which is communicated through the slip rings 150 and transmit/receive switch 148 to the receiver 152. The electric signal is processed by the computer 144 and displayed by the display unit 122. Typically three dimensional image information is generated from the signals processed by the computer 144.

Figure 7:
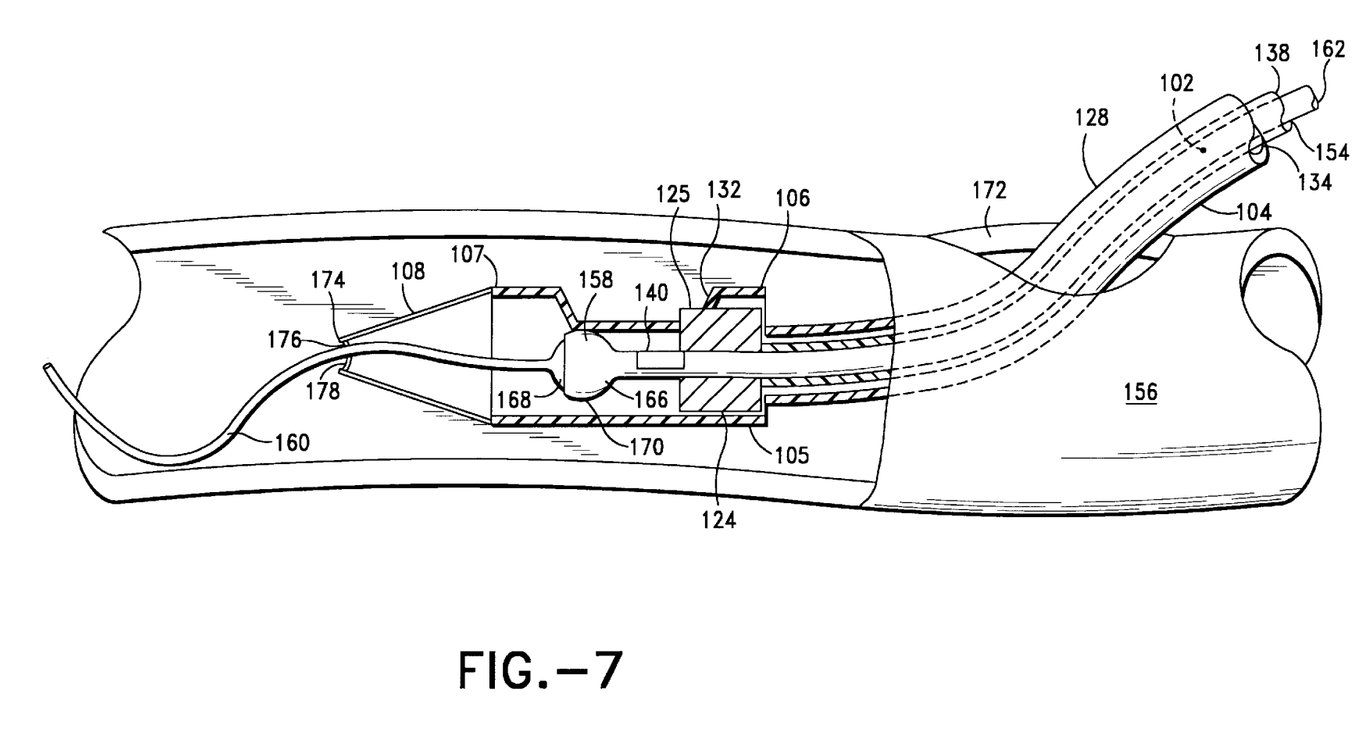
FIG. 7 is a cut-away view of the distal end of the articulated guidewire and the distal end of the catheter device of FIG. 5 inserted into a biological conduit.

With particular reference to FIG. 7, there is shown the distal end 128 of the catheter body 104 inserted through the slit 172 of the blood vessel 156. The sensor 140 aligns with the opening 132 of the housing 106. The opening 132 facilitates sensory communication between the sensor 140 and the interior of the blood vessel 156 when the sensor 140 aligns with the opening 132.

The nosecone 108 has a nosecone opening 174 and a diaphragm 176. The diaphragm 176 mounts at the distal end 107 of the housing 106 over the nosecone opening 174 to form a seal. The diaphragm 176 is flexible, having an annular shape and a central opening 178. The diaphragm 176 seals about the articulated guidewire 102 when the articulated guidewire 102 passes through the central opening 178. The diaphragm 176 prevents solids or fluids (e.g. biological tissue) from passing through the distal end 107 of the housing 106.

Figure 8:
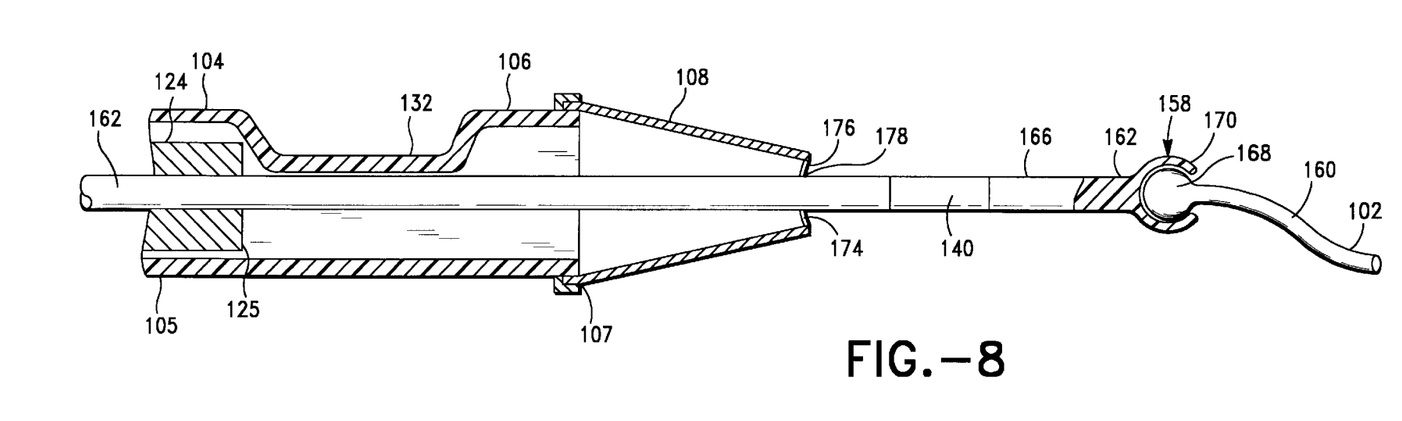
FIG. 8 is a partial cross section of the distal end of a catheter device and the articulated guidewire of FIG. 5.
Figure 9:
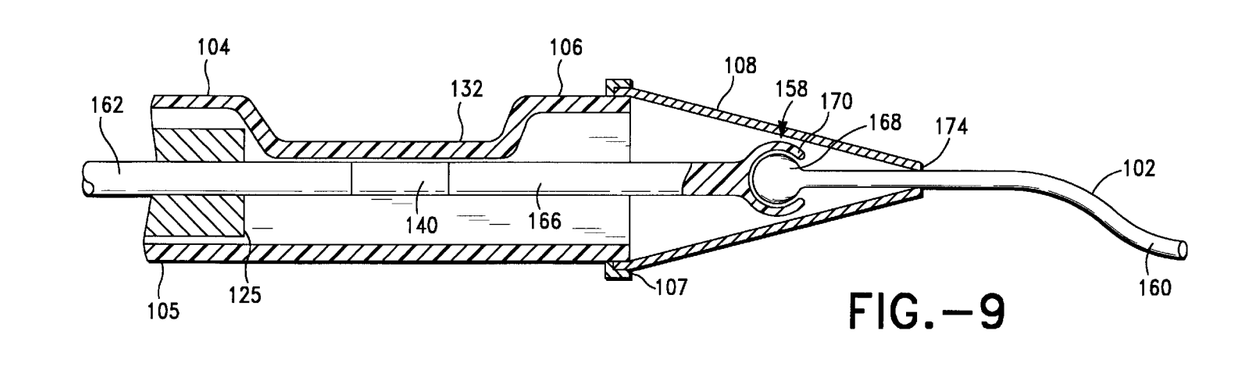
FIG. 9 is a partial cross section of the distal end of a catheter device and the articulated guidewire of FIG. 5.

With reference to both FIG. 8 and FIG. 9, the articulated guidewire 102, the distal end 128 of the catheter body 104 and the housing 106 are shown. The catheter body 104 and the housing 106 surround the sensor cable 162 of the articulated guidewire 102.

With particular reference to FIG. 8, there is shown the housing 106 in a first position wherein the sensor 140 extends beyond the nosecone 108. Accordingly, with one full rotation of the sensor cable 162, the sensor 140 rotates to sense an area defined along a 360 degree arc.

With particular reference to FIG. 9 there is shown the housing 106 in a second position wherein the opening 132 of the housing 106 aligns with the sensor 140. The catheter body 104 is capable of tracking over the sensor cable 162 between the first position (FIG. 8) and the second position to selectively align the sensor 140 with respect to the housing 106. When the sensor 140 aligns with the opening 132, signals can be communicated from the sensor 140 via the opening 132 at an angle defined by the opening 132 as the sensor 140 rotates.

In Use:

The articulated guidewire 102 can be used to sense the interior of a biological conduit. The articulated guidewire 102 is particularly useful in conjunction with catheters which insert into the human body. Various biological conduits in the human body are able to receive the articulated guidewire 102. The urinary tract, digestive tract and blood vessels are examples of such biological conduits.

Various functions of the articulated guidewire 102 are illustrated by the following example which describes some uses of the articulated guidewire 102 in conjunction with an atherectomy catheter body 104.

When opening 172 is prepared in a suitable blood vessel (FIG. 2) such as the femoral artery, the articulated guidewire 102 slides into the blood vessel 156. The articulated guidewire 102 extends coaxially through a portion of the blood vessel 156 and articulated guidewire 102 flexes to conform to the geometry of the blood vessel 156. The articulated guidewire 102 moves into a desired location such as near an occlusion in the coronary artery.

The articulated guidewire 102 rotates to image the interior of the blood vessel 156. The articulated guidewire 102 slides into a desired location within the vasculature and aligns the sensor 140 with selected areas to be imaged. Images are electronically communicated from the sensor 140, along the articulated guidewire 102, through the instrumentation cable 118, to the computer 144 and the display unit 122 (FIG. 6). An image representing the interior of the imaged area is displayed on the display unit 122 to facilitate assessment of the condition of the imaged area. From the diagnosis, the necessity of inserting a catheter device to perform an atherectomy is determined.

If an atherectomy is unnecessary, the sensor 140 can be moved through the vasculature for additional imaging, or the sensor 140 can be removed. If an atherectomy is necessary, an atherectomy catheter body 104 is then inserted into the blood vessel 156 along the articulated guidewire 102 to the location of atheroma to be captured and removed by the atherectomy catheter 104. The atheroma is then removed.

The sensor 140 continues operation during the atherectomy procedure. The sensor 140 of the articulated guidewire 102 is operable independently of the housing 106. For example, the sensor 140 aligns within the opening 132 region of the housing 106 to direct energy through the opening 132. Alternatively, the sensor 140 extends, with the articulated guidewire 102, beyond the distal end of the nosecone 108 to image over a 360 degree arced path.

After completion of the atherectomy procedure, the sensor 140 continues to operate. By observing the display unit 122, an operator can determine the effectiveness of the completed atherectomy. Additional areas where tissue removal is desirable can be identified and explored.

The articulated guidewire 102 is removed from the blood vessel when imaging is no longer desired. During removal of the articulated guidewire 102, however, imaging can continue. In this way, an operator can re-inspect the interior of the blood vessel 156. Finally, the articulated guidewire 102 is completely removed from the vasculature.

The foregoing detailed description has described various aspects of a preferred embodiment of the articulated guidewire 102. It is to be understood that the above description is illustrative only and not limiting of the disclosed invention. Particularly, the specific details of the connector 158 can differ from those illustrated and described so long as the connector 158 permits the sensor cable 162 to rotate and align with respect to the satellite wire 160. It will be appreciated that the shape and operation of the satellite wire 160 can differ from that disclosed so long as the satellite wire 162 securely holds the sensor cable 162 in a desired position for rotation. Although specific details are disclosed as stated above, the scope of the present inventive concept is to be limited only by the claims set forth below.

We claim:

1. A catheter device having an articulated guidewire for insertion into a biological conduit, comprising:

a catheter body formed with a housing;

a sensor cable having a proximal end and a distal end, the sensor cable being rotatable, the sensor cable extends through the catheter body and the housing;

a sensor attached to the sensor cable adjacent the distal end, the sensor rotates with the sensor cable;

a flexible connector attached to the distal end of the sensor cable; and a satellite wire attached to the connector, whereby when the sensor cable rotates the sensor, the satellite wire remains stationary.

2. A device as set forth in claim 1, wherein the housing includes an opening and a nose cone, the sensor cable moves from a first position wherein the sensor aligns with the opening to a second position wherein the sensor is not aligned with the opening.

3. A device as set forth in claim 2, wherein the sensor cable occupies the second position, the articulated guidewire extends through the nose cone of the housing to position the sensor beyond the nose cone.

4. A device as set forth in claim 2, wherein the nose cone includes a diaphragm, the diaphragm forms a seal between the articulated guidewire and the nosecone.

5. A device as set forth in claim 2, wherein the sensor occupies the first position, the satellite wire extends through the nose cone and into the biological conduit.

6. A device as set forth in claim 4, wherein the sensor occupies the first position, the satellite wire extends distally through the nose cone and into the biological conduit; and when the sensor occupies the second position, the sensor is positionable distal to the nose cone.

7. A device as set forth in claim 1, wherein:

the housing includes a lateral window and a nose portion, the nose portion comprising at least one diaphragm defining an orifice;

the sensor cable is movable axially from a first position wherein the sensor is aligned with a portion of the lateral window, the connector is proximal to a diaphragm, and the satellite wire extends distally through a diaphragm orifice;

to a second position wherein the sensor is proximal to a diaphragm and the connector is distal to a diaphragm;

to a third position wherein the sensor is distal to a diaphragm.

8. An articulated guidewire for insertion into a biological conduit, comprising:

a sensor cable having a proximal end and a distal end, the sensor cable being rotatable;

a sensor attached to the sensor cable adjacent the distal end, the sensor rotates with the sensor cable;

a flexible connector attached to the distal end of the sensor cable; and a satellite wire attached to the connector, whereby when the sensor cable rotates the sensor, the satellite wire remains stationary.

9. A device as set forth in claim 8, wherein the connector includes a ball attached to the satellite wire and a socket attached to the distal end of the sensor cable to permit the satellite wire and the distal end of the sensor cable to align at a variable angle, the ball rotatably interconnects with the socket to permit rotation of the sensor cable with respect to the satellite wire.

10. A device as set forth in claim 8, wherein the connector includes a ball attached to the distal end of the sensor cable, the satellite wire has a socket, the ball rotatably interconnects with the socket to align the distal end of the sensor cable and the satellite wire to align at a variable angle and to permit rotation of the sensor cable with respect to the satellite wire.

11. A device as set forth in claim 8, wherein the sensor cable is fabricated from electrically conductive material.

12. A device as set forth in claim 8, wherein the sensor circumscribes the sensor cable.

13. A device as set forth in claim 8, wherein the sensor is a PVDF ultrasonic sensor.

14. An articulated guidewire for insertion into a biological conduit having an interior, comprising:

a sensor cable having a proximal end and a distal end, the sensor cable being rotatable;

a sensor connected with the sensor cable near the distal end, the sensor rotates with the sensor cable;

a connector including a ball and socket joint, the connector attaches to the distal end of the sensor cable;

a satellite wire attached to the connector for holding the distal end of the sensor cable with respect to the biological conduit, whereby, when the articulated guidewire inserts into the biological conduit, the satellite wire holds the distal end of the sensor cable with respect to the biological conduit and the sensor cable rotates the sensor independently of the satellite wire.

15. A device as set forth in claim 14, wherein the sensor cable is formed having a diameter within the range of 0.018–0.020 inches.

16. A device as set forth in claim 14, wherein the connector has a maximum diameter of less than 0.028 inches.

17. A device as set forth in claim 14, wherein the satellite wire has a diameter within the range of 0.010–0.014 inches.

* * * * *

UNITED STATES PATENT AND TRADEMARK OFFICE
CERTIFICATE OF CORRECTION

PATENT NO.      : 6,355,005 B1
DATED           : March 12, 2002
INVENTOR(S)     : Ferolyn T. Powell et al.

It is certified that error appears in the above-identified patent and that said Letters Patent is hereby corrected as shown below:

<u>Title page,</u>
Item [73], Assignee, change "Devices for Vascular Intervention, Inc.", to read
-- Advanced Cardiovascular Systems, Inc. --.
Item [56], U.S. PATENT DOCUMENTS, change "5,964,016", to read -- 5,464,016 --.

Signed and Sealed this

Twenty-fourth Day of December, 2002

JAMES E. ROGAN
*Director of the United States Patent and Trademark Office*